(12) United States Patent
Brunnberg et al.

(10) Patent No.: US 8,062,255 B2
(45) Date of Patent: Nov. 22, 2011

(54) AUTO-INJECTOR

(75) Inventors: Lennart Brunnberg, Tyresö (SE); Jakob Wikner, Täby (SE)

(73) Assignee: SHL Group AB, Nacka Strand (SE)

( * ) Notice: Subject to any disclaimer, the term of this patent is extended or adjusted under 35 U.S.C. 154(b) by 407 days.

(21) Appl. No.: 11/949,947

(22) Filed: Dec. 4, 2007

(65) Prior Publication Data
US 2008/0147006 A1 Jun. 19, 2008

Related U.S. Application Data

(60) Provisional application No. 60/869,772, filed on Dec. 13, 2006.

(30) Foreign Application Priority Data

Dec. 13, 2006 (EP) ..................................... 06125980

(51) Int. Cl.
*A61M 5/20* (2006.01)
(52) U.S. Cl. ...................................................... 604/136
(58) Field of Classification Search .................. 604/187, 604/134–137, 181, 165.01–165.03, 192–198, 604/68, 110, 131, 132, 133, 156
See application file for complete search history.

(56) References Cited

U.S. PATENT DOCUMENTS

| 3,656,472 | A | * | 4/1972 | Ben Moura | 600/576 |
| 4,900,311 | A | * | 2/1990 | Stern et al. | 604/198 |
| 5,478,316 | A |  | 12/1995 | Bitdinger et al. |  |
| 6,585,685 | B2 | * | 7/2003 | Staylor et al. | 604/68 |
| 2001/0044847 | A1 | * | 11/2001 | Kirchhofer et al. | 709/227 |
| 2005/0261634 | A1 | * | 11/2005 | Karlsson | 604/197 |
| 2005/0288633 | A1 | * | 12/2005 | Jeffrey | 604/110 |
| 2008/0077090 | A1 | * | 3/2008 | Hommann | 604/135 |

FOREIGN PATENT DOCUMENTS

| EP | 1 349 590 B1 |  | 5/2006 |  |
| WO | 02/47746 A1 |  | 6/2002 |  |
| WO | WO2006/086899 | * | 8/2006 | 604/135 |

* cited by examiner

*Primary Examiner* — Christopher D Koharski
(74) *Attorney, Agent, or Firm* — Potomac Patent Group PLLC

(57) ABSTRACT

A device for delivering a dose of medicament includes a generally elongated housing, a container containing medicament to be injected through a needle, a force device acting on the container and capable of, upon activation, moving the container and the needle for penetration and subsequently expelling medicament through the needle, and an activating device arranged to activate the force means. The activating device includes a needle shield slidably arranged in relation to the housing, which upon movement releases the force device, and a release device arranged in the front, injecting, area of the device, which, when in a non-activated state prevents the needle shield from sliding, thereby preventing activation, and when activated, enables sliding of the needle shield and thereby activation of the device. The release device is arranged on the device such that it promotes an ergonomic grip of the device for its activation.

11 Claims, 5 Drawing Sheets

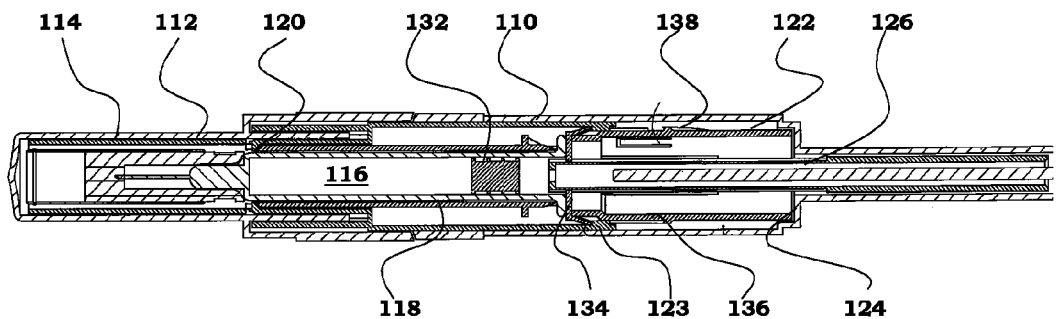
Fig. 6
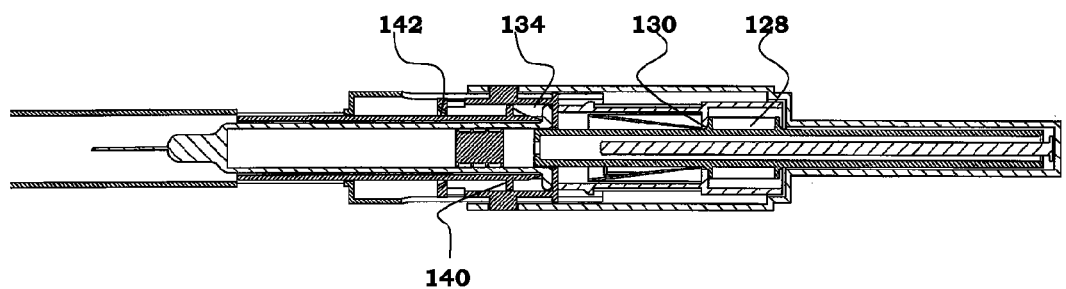
Fig. 7
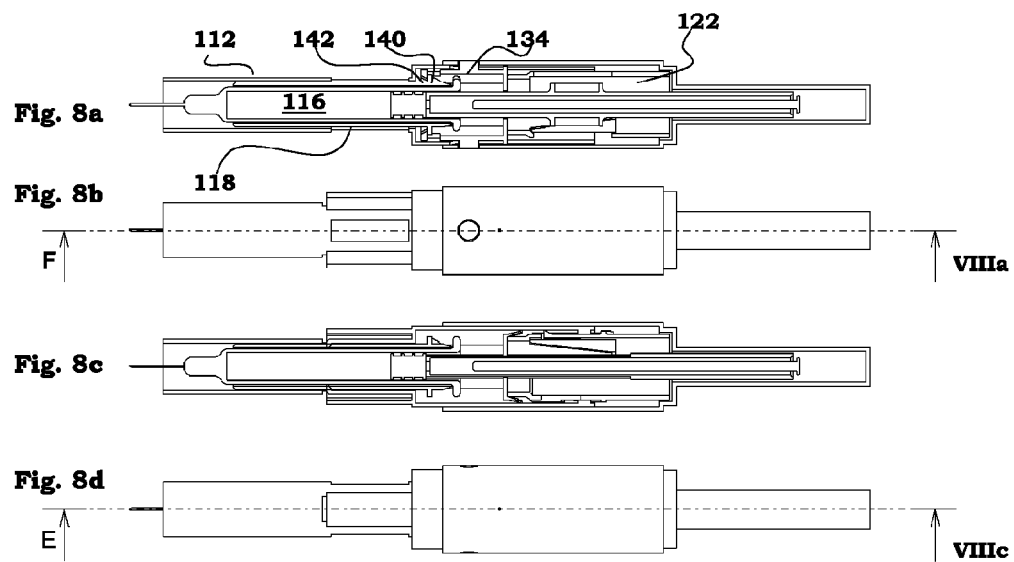
Fig. 8a
Fig. 8b
Fig. 8c
Fig. 8d

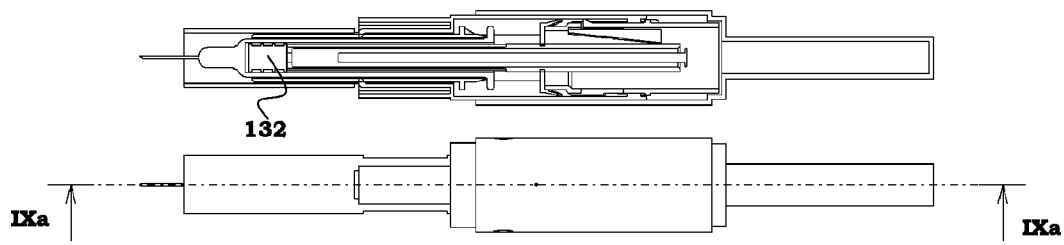
Fig. 9a
Fig. 9b
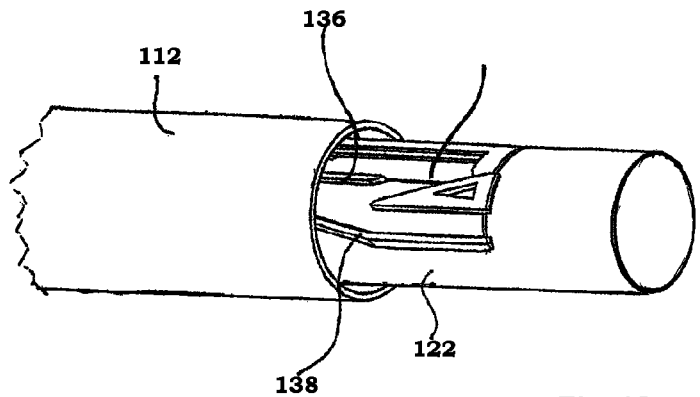
Fig. 10
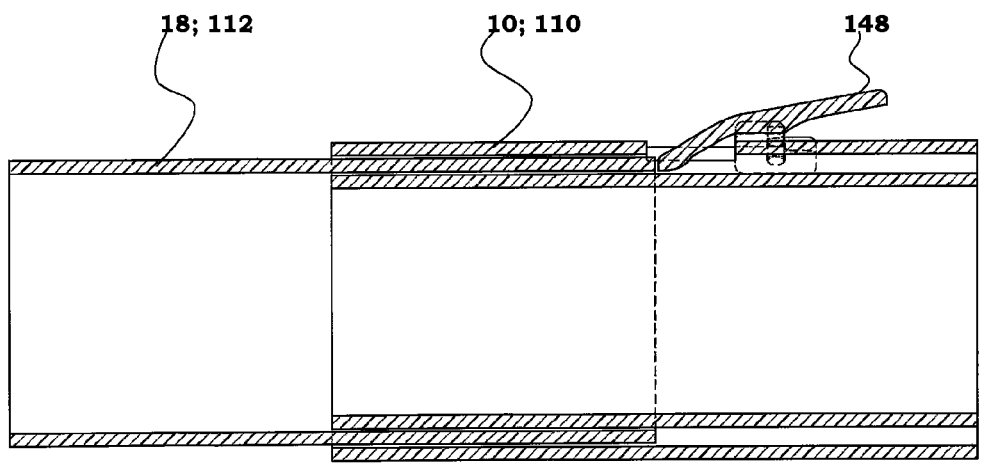
Fig. 11

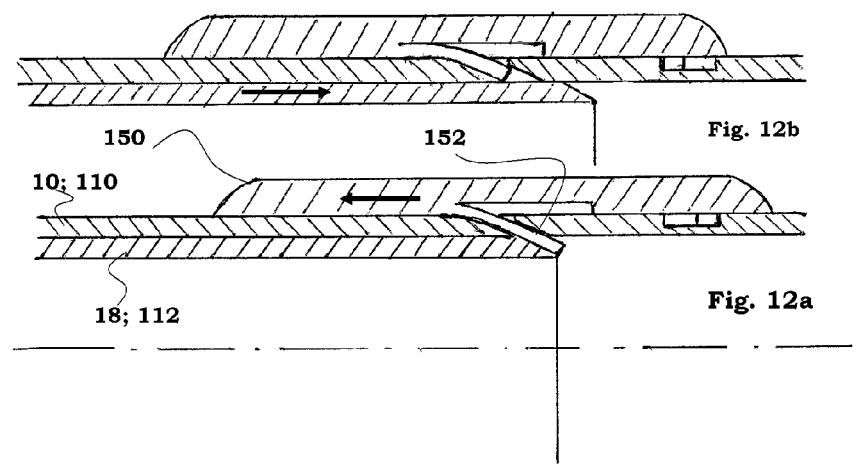
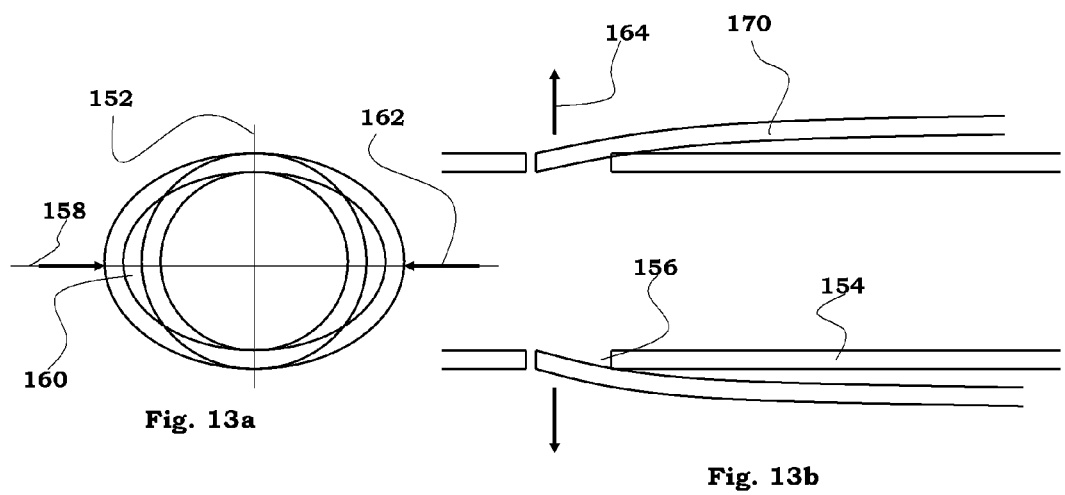

AUTO-INJECTOR

The present invention relates to an auto-injector comprising needle shield activation of the penetration and subsequent injection.

BACKGROUND

For many patients using injecting devices for self-administration of medicament, there is a discomfort to handle the device, especially regarding the penetration. For many users there is a mental resistance against self-penetration. Other users also have a general fear of needles which enhances the discomfort and negative feeling of self-administration.

It is further desirable for many patients that the number of actions that the patient needs to perform in order to receive a dose of medicament is held as low as possible, on the one hand regarding handling of the device and on the other hand the functionality of the device.

One such device is disclosed in patent EP 1349590 B by SHL MEDICAL AB (2003-10-08) describing an injector having a number of features that facilitate the handling of the injector. The penetration and injection is performed automatically by pressing a button on the upper end of the injector. When the injection is performed the injector is withdrawn whereby a needle shield extracts around the needle in a locked way. As an additional safety aspect, the activation cannot be performed unless the injector is pressed against an injection site, i.e. a two-step operation to activate the injector is required.

Another type of injecting device is shown in U.S. Pat. No. 5,478,316 by BECTON DICKINSON CO (1995-12-26) disclosing a high degree of automatic functions. When a sleeve at the front injection end of the injector, being the needle shield, is pressed against an injection site, the sleeve is moved a certain distance into the injector. The movement enables a push button arranged about midway on the side of the injector housing to be pressed by the user. This in turn releases a constant spring means acting on a driver and rod unit in contact with a syringe assembly so that a penetration is performed. When a certain penetration depth is reached, the driver is disconnected from the rod and the rod is urged further by the spring, causing an injection of medicament into the injection site. After the injection is completed the device is withdrawn from the injection site, whereby the sleeve moves forward, covering the needle.

Another aspect of injectors is the human aspect of handling the injector regarding how it is held during operation. A general aim is to have the patient holding the injector in an ergonomic way that may permits the penetration and injection in different locations on the body, such as around the waist and also on the backside of the waist and/or in the buttocks of the patient. The patient does not see the injector at those locations and need to be able to hold the injector without having to change grip. One suitable ergonomic grip for many locations is e.g. the pen grip, whereby the user holds the injector in the front, injection area. This could be difficult when the injector has push buttons on the distal end of the injector or slide buttons on the side of the injector.

SUMMARY

An aim of the present invention is to provide an injector having a high degree of functionality, that is easy to use and reliable, and which preferably provides a level of handling freedom for each patient.

This aim is obtained by the features of the independent patent claim. Preferable embodiments of the invention are subject of the dependent patent claims.

According to an aspect of the invention, there is provided a device for delivering a dose of medicament, comprising a generally elongated housing, a container containing medicament to be injected through a needle, force means acting on the container and capable of, upon activation, moving the container and the needle for penetration and subsequently expelling medicament through the needle, activating means arranged to activate the force means, wherein the activating means comprises a needle shield slidably arranged in relation to the housing, which upon movement releases the force means, release means arranged in the front, injecting, area of the device, which, when in a non-activated state prevents the needle shield from sliding, thereby preventing activation, and when activated, enables sliding of the needle shield and thereby activation of the device, and the release means is arranged on the device such that it promotes an ergonomic grip of the device for its activation.

The release means may comprise at least one button to be activated in order to enable movement of the needle shield, and two or possibly more buttons arranged such that it guides a user to hold the device like a pen for activation. The button(s) also increase(s) the degree of safety and ergonomics.

The button(s) can be push buttons, sliding buttons or arranged as a sleeve slidable in relation to the housing.

The sleeve is preferably slidable in a forward direction from a non-activated state to an activated state, thereby enabling sliding of the needle shield.

According to a further aspect of the invention, the force means comprises a plunger rod and a compression spring acting on the plunger rod, which acts on a stopper arranged in the container.

According to yet another aspect of the invention, the activating means comprises flexible locking means arranged to hold the plunger rod with the compression spring in a tensioned state, which flexible locking means are released when the needle shield is moved a certain distance, releasing the plunger rod.

According to an alternative aspect of the invention, the activating means comprises stop ledges co-acting with ledges on the plunger rod to hold the plunger rod with the compression spring in a tensioned state, which stop ledges are arranged on a rotatable component and means arranged on the needle shield capable of rotating the rotatable component when the needle shield is moved a certain distance, rotating the stop ledges out of contact with the ledges on the plunger rod, releasing the plunger rod.

The needle shield may be arranged with protrusions co-acting with inclined ridges on the rotatable component causing the rotatable component to rotate when the needle shield is moved.

According to a further aspect of the invention, it further comprises means for pushing the needle shield to an extended position, and in some cases beyond the initial position, covering the needle when the device is withdrawn from an injection site, and means for locking the needle shield in the extended position.

The device according to the present invention presents a number of advantages. For example, there is a high degree of functionality and automation since the activation of the injector, comprising both penetration and injection is enabled by the needle shield when pushing the injector against the injection site. This causes the needle shield to slide a distance, whereby the injector is activated.

The discomfort of having to penetrate manually by the user is thus removed. The only manual action that the patient needs to perform is to withdraw the injector from the site. During withdrawal, the needle shield is pushed out and covers the needle, and also locks in the extended state, thereby preventing unintentional needle sticks.

A reliable and functional injector is provided because one compression spring in cooperation with a plunger rod, performs both the penetration and subsequent injection, thus also reducing the number of components of the injector. The plunger rod is held with the compression spring in a tensioned state when delivered to the user, whereby no additional operations, apart from removing a protection cap, need to be performed in order to have the injector ready for injection.

In order to elevate the safety aspect of the injector and also provide a freedom of handling and holding of the injector during its use, release means are arranged at the front, injection, end of the device. When the release means are not activated, they prevent the needle shield from being moved and thus the injector can not be activated. When the release means are activated, e.g. by pushing or sliding buttons by the fingers of the user, the needle shield can slide into the housing and activate the device. Because the release means are arranged at the front end of the injector, this promotes the user to hold the injector as a pen, which is desirable for many applications and drugs.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 6 is a side view of another embodiment of the present invention in cross-section, FIG. 7 is a side view of the embodiment of FIG. 6 in a cross-section taken 90° in relation to FIG. 6, FIGS. 8a-8d and 9a-9b show the embodiment according to FIG. 6 in different operational positions, FIG. 10 is a detailed view of the embodiment according to FIG. 6, FIG. 11 is a detailed view of a release means comprised in the present invention, FIG. 12 a-b are detailed views of another release means comprised in the present invention, and FIG. 13 a-b are detailed views of a further release means comprised in the present invention.

DETAILED DESCRIPTION

Figure 1:
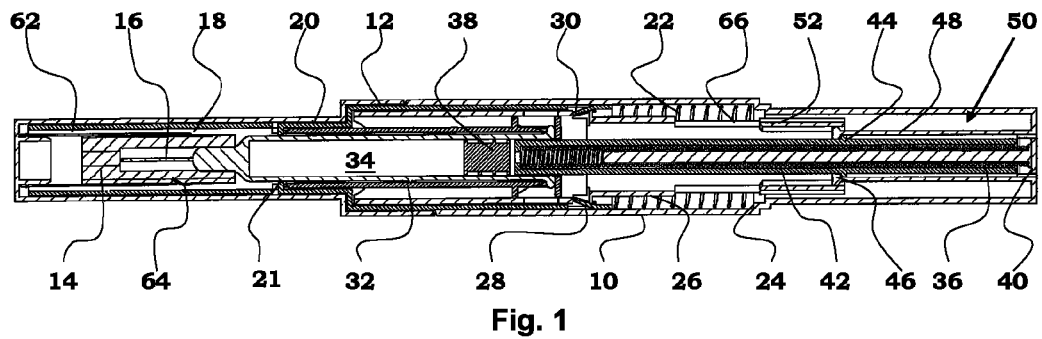
FIG. 1 is a side view of a first embodiment of the present invention in cross-section.
Figure 2:
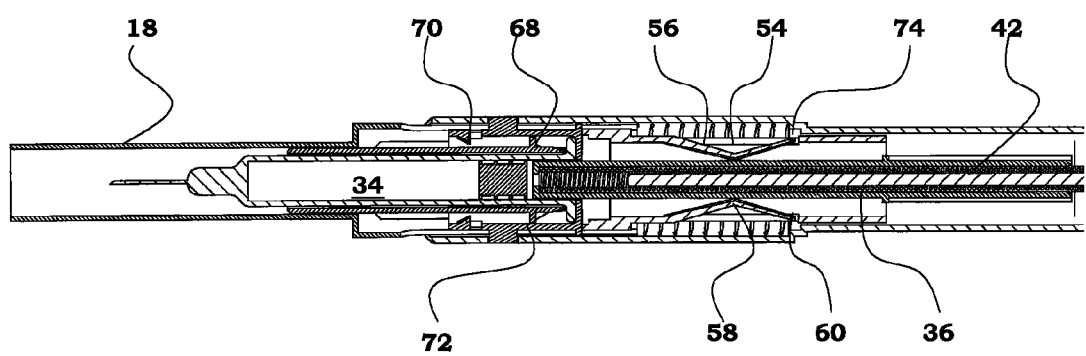
FIG. 2 is a side view of the embodiment of FIG. 1 in a cross-section taken 90° in relation to FIG. 1, FIGS. 3a-3d, 4a-4d and 5a-5d show the embodiment according to FIG. 1 in different operational positions.
Figure 3A:
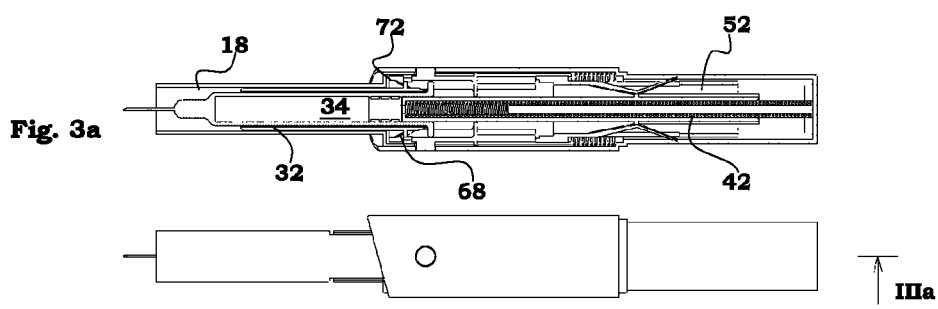
Figure 3B:
Figure 3C:
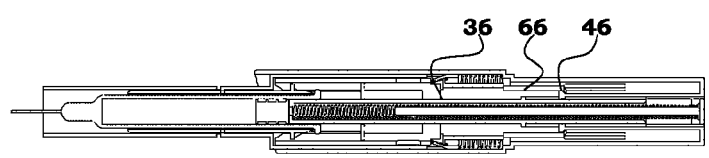
Figure 3D:
Figure 4A:
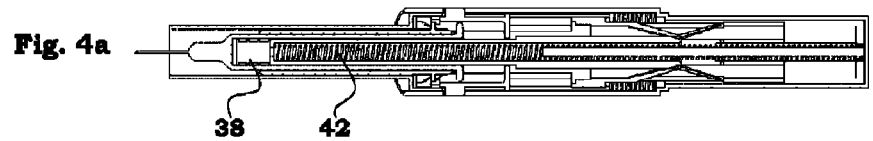
Figure 4B:
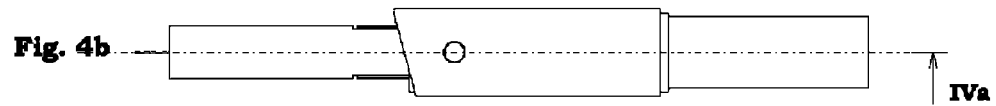
Figure 4C:
Figure 4D:
Figure 5A:
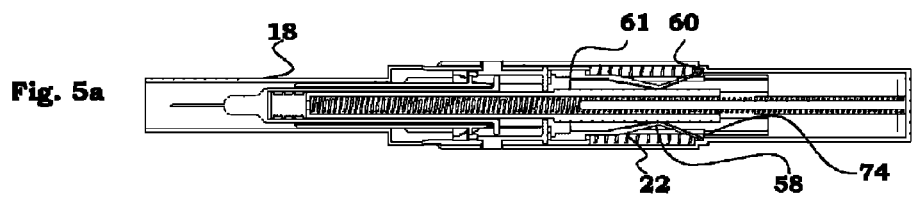
Figure 5B:
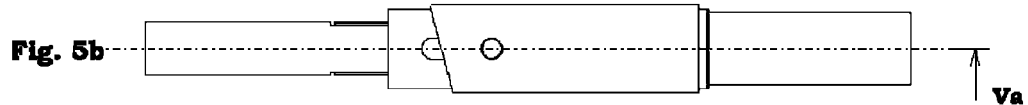
Figure 5C:
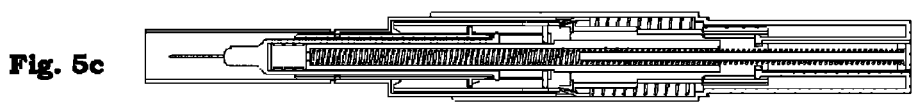
Figure 5D:
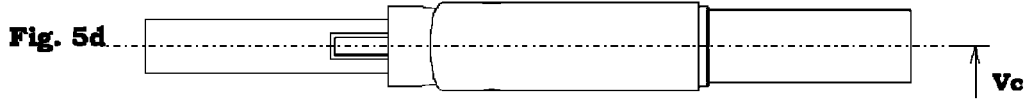

FIGS. 1 and 2 show one embodiment of the present invention. It comprises a generally tubular elongated outer housing 10 having a front end, to the left in the figures, to be placed at the injection site of a patient. When the injector is delivered to a user it is arranged with a protective cap 12 at its front end. To the protective cap a needle sheath is attached, which needle sheath 14 surrounds and protects an injection needle 16. Inside the front cap a tubular needle shield 18 is arranged surrounding the needle. At a mid part of the needle shield, a pair of tongues 20 is arranged having inwardly protruding ledges 21. The needle shield further extends up along the inner surface of the housing. A needle shield spring 22 is arranged between the distal end surface of the needle shield and a ledge 24 on the inner surface of the housing. Inside the needle shield a tubular member 26 is arranged, hereafter named needle shield link. It is connected to the needle shield via inwardly extending tongues 28 on the needle shield that fit into recesses 30 in the needle shield link.

Inside the needle shield link a medicament container holder 32 is slidably arranged, as will be described in more detail below. Inside the container holder a medicament container 34 e.g. a cartridge, a syringe or the like; is attached, which then also is slidable. The container holder is held from moving forward by the ledges 21 on the needle shield. A plunger rod 36 is arranged between a stopper 38 of the container and a distal end wall 40 of the housing. Inside the plunger rod a compression spring 42 is arranged between a front end wall of the plunger rod and the distal end wall of the housing. At a certain distance from the front end of the plunger rod, it is arranged with oppositely placed, outwardly protruding ledges 44. In the start position, these ledges abut inwardly protruding ledges 46 arranged on arms 48 on an inner tubular structure 50 of the housing. The arms are held in this position by the rear, tubular part of the needle shield link. The needle shield link is further arranged with two elongated, oppositely arranged, slots 54, FIG. 2, in which arms 56 are attached. The arms have an inwardly inclined first direction and an outwardly inclined second direction, where the transition 58 between the sections is in contact with the plunger rod. The free ends 60 of the arms are in the slots. The upper, rear end of the plunger rod is arranged with a thicker section, FIG. 2.

The device is intended to function as follows. When the device is delivered, it is arranged with the protective cap 12 mounted on the front end of the device. When a user is to administer a dose of medicament, the cap is removed. An inner sleeve 62 of the cap is arranged with a hook 64 that grips into the resilient needle sheath 14, so that when the cap is removed so is also the needle sheath. The syringe housing and the syringe are prevented from being pulled out when the cap is removed due to the inwardly directed ledges 21 holding the syringe holder.

When the cap is removed the delivery device is ready for use, FIG. 2. The user presses the front end of the needle shield 18 against the injection site whereby the needle shield is pushed into the housing. Because the needle shield is connected to the needle shield link, also the latter is pushed rearwards. When the needle shield link 26 has been pushed a certain distance, the ledges 46 holding the plunger rod 36 will pass the narrower tubular part 52 of the needle shield link and move into two elongated slots 66 in the needle shield link. This allows the arms to flex outwardly thereby releasing the plunger rod.

The plunger rod now moves forward due to the force from the compression spring 42, pressing on the stopper 38 of the container 34. Due to the incompressibility of the medicament in liquid form, the container 34 and container holder 32 are moved forward. This is enabled in that the inwardly directed ledges 21 of the needle shield, that previously held the container holder in place, are now free to flex outwardly. Thus a penetration into the tissue of the patient is performed, FIG. 3. The movement of the container holder, and thus the penetration, is stopped when an annular ledge 68 of the container holder comes in contact with inwardly directed ledges 70 of a component 72, called syringe housing, attached to the housing.

The force of the compression spring on the plunger rod causes the latter to move the stopper 38 forward, thereby injecting medicament through the needle 16 and into the tissue of the patient. The injection is stopped when the stopper abuts the front end wall of the container, FIG. 4.

The injection is now completed and the device can be withdrawn from the injection site. This enables the needle shield 18 to move back out again with the help of the needle shield spring 22. During the previous injection of medicament, the plunger rod moved forward, and during this movement the enlarged rear part 61 of the plunger rod came in contact with the transition 58 of the inclined arms 56, urging the free end 60 of the arms out of the sleeves and in contact with the inner surface of the housing. When the needle shield now has been moved out again the free ends of the arms will be pushed past a circumferential ledge 74 of the housing. This will lock the needle shield in the extracted position, which is extended further than the initial position, because the free ends of the arms will come in contact with the circumferential ledge and prevent any inwardly movement, FIG. 5. By this any accidental needle sticks of the used needle are prevented.

FIGS. 6-10 show another embodiment of the present invention. The injecting device comprises a generally tubular main body 110. A needle shield 112 is arranged slidably inside the main housing. A protective cap 114 is arranged in the same manner as the previous embodiment. Also here a container 116 attached to a container holder 118 are held in place by inwardly extending ledges 120 on arms of the needle shield, which arms are held from flexing outwards by the cap. Inside the housing a generally tubular member 122, hereafter named rotator, is rotationally and slidably arranged at the rear part of the needle shield. It is arranged with a number of ridges and knobs 123 on its outer surface which are to cooperate with guide members arranged on the inner surface of the needle shield, the function of which will be explained below.

The upper end surface of the rotator 122 is in contact with a wall surface 124 of the housing, preventing longitudinal movement but allowing rotational movement between them. Inside the rotator, a plunger rod 126 is slidably arranged and movable with the help of a compression spring (not shown). The upper part of the plunger rod is arranged with a number of outwardly extending stop members 128, FIG. 7, arranged to cooperate with inwardly extending stop members 130 on the inner surface of the rotator, as will be explained below. The front end of the plunger rod is in contact with a stopper 132 arranged inside the container. The lower end surface of the rotator is in contact with an end wall of a component, syringe housing 134, attached to the housing. A needle shield spring (not shown) is arranged to press on the needle shield between a ledge on the housing and on the upper end surface of the needle shield.

The device is intended to function as follows. When the device is assembled and delivered to the user the protective cap 114 is covering the front end with the needle shield 114. The plunger rod 126 is in its rearmost position and the injection spring is tensioned. The plunger rod is held in this position by a set of oppositely arranged outwardly extending knobs 128, on the plunger rod abutting a set of ledges 130 arranged on the inner surface of the rotator.

When the patient is to use the device the protective cap is removed and in the same manner as with the previous embodiment, the needle sheath is also removed, FIG. 7. The device is now ready for injection. The needle shield 112 is pressed against the injection site and the needle penetrates the skin. During the inward movement of the needle shield the guide knobs 123 of the needle shield run along longitudinally extending ridges 136, until they come in contact with inclined ledges 138, FIG. 6. The contact between these causes the rotator to turn during further movement of the needle shield. The rotator is thus turned until the outwardly extending knobs 128 of the plunger rod 126 slip off the ledges 130 arranged on the upper part of the rotator, thereby starting the penetration. The plunger rod moves downward due to the force of the injection spring and the knobs 123 run in longitudinal grooves on the inner surface of the rotator. The movement of the plunger rod causes the container 116 with the container holder 118 to move forward due to the incompressibility of the medicament inside the container, causing a penetration, FIG. 8. The movement of the container is stopped when an annular ledge 140 on the outer surface of the container holder abuts inwardly extending ledges 142 of the container housing 134. The further movement of the plunger moves the stopper, whereby medicament is injected through the needle, until the stopper abuts the front end wall of the container.

When the injection is finished, the user removes the device from the injection site, whereby the needle shield 112 moves into an extended position due to the force of the needle shield spring. The guide knobs 123 of the needle shield now move along the other side of the ridges 136 and at a certain position along this path, when the needle shield is in its most extended position covering the needle, the guide knobs fit into recesses in the rotator, thereby locking the needle shield in the extended position, preventing the needle shield to be pushed in again. The risk of unintentional needle sticks is thus eliminated.

In order to further enhance the safety of the device and to also ensure that the patient holds the injector in a proper way, the injector can be provided with release means. The release means could comprise locking members that when inactivated locks the needle shield 18; 112 in the initial retracted position. According to one embodiment, FIG. 11, the release means could comprise push buttons 148 arranged at the front of the injector. They are preferably placed there in order that the patient uses an ergonomic grip e.g. pen like grip, to hold the injector. In this aspect, there could be two buttons that need to be operated, one on each side of the injector.

According to another embodiment, the release means could comprise a sleeve 150, FIG. 12, arranged at the front end of the injector, which is slidable in the elongated direction of the injector for releasing the needle shield. For releasing the needle shield, the sleeve is preferably moved in the forward direction when the patient presses the injector against the injection site. This causes a flexible locking member 152 protruding through the housing to move from a position where it blocks the needle shield from moving into the housing, FIG. 12a, to a position where the locking member has been moved into the wall of the housing, freeing the needle shield, FIG. 12b. Apart from push buttons and sleeves, also other release members are feasible, such as sliding buttons.

A further example of release means is shown in FIG. 13. In this case the front end of a housing 170 is made somewhat elliptic in cross-section with a shorter axis 152 that is generally equal to the diameter of the needle shield 154, where the needle shield is arranged with slots 156 in which the end surface of the housing at the shorter axis fit, whereby the needle shield is locked from movement. The longer axis 158 of the ellipse is larger than the diameter of the needle shield, creating a space 160 between the housing and the needle shield on both sides.

When a user presses in the area of the longer axis in a radial direction, as indicated with arrows 162, which area preferably is marked in some way, like different colour for visual detection or grooves, indentations and the like for tactile detection, the housing at the shorter axis will flex radially outwards, as indicated by arrows 164, whereby the housing moves out of the slots of the needle shield, thereby freeing it for movement, as described above.

Even though the embodiments described above are intended to handle single chamber single dose containers, it is to be understood that the invention could be modified to handle other types of containers such as dual chamber containers that need mixing and priming before injection, and/or dose size setting means. Instead of one single spring performing both penetration and injection, several independent acting springs may be utilized for penetration and subsequent injection.

It is thus to be understood that the embodiments described above and shown in the drawings are to be regarded only as non-limiting examples of the present invention and that it may be modified within the scope of the patent claims.

What is claimed is:

1. A device for delivering a dose of medicament, comprising:
    a generally elongated housing having a front end and a rear end,
    a container containing medicament to be injected through a needle,
    force means comprising a plunger rod and a compression spring arranged within the plunger rod, wherein the plunger rod is arranged to act on a stopper disposed in the container such that, upon activation of the force means, the container and the needle are moved for penetration and for subsequently expelling medicament through the needle, and
    activating means comprising a needle shield slidably arranged in relation to the housing, which upon movement releases the force means, wherein the elongated housing is elliptic in cross-section and has a short axis and a long axis, and the needle shield is arranged with slots in which fit a front end surface of the housing at the short axis, whereby the needle shield is locked from movement, wherein the activating means comprises stop ledges co-acting with ledges on the plunger rod to hold the plunger rod with the compression spring in a tensioned state, which stop ledges are arranged on a rotatable component and means arranged on the needle shield capable of rotating the rotatable component when the needle shield is moved a certain distance, rotating the stop ledges out of contact with the ledges on the plunger rod, releasing the plunger rod.

2. The device of claim 1, wherein the needle shield is arranged with protrusions co-acting with inclined ridges on the rotatable component causing the rotatable component to rotate when the needle shield is moved.

3. A device for delivering a dose of medicament, comprising:
    a generally elongated housing having a front end and a rear end,
    a container containing medicament to be injected through a needle,
    force means comprising a plunger rod and a compression spring arranged within the plunger rod, wherein the plunger rod is arranged to act on a stopper disposed in the container such that, upon activation of the force means, the container and the needle are moved for penetration and for subsequently expelling medicament through the needle, and
    activating means comprising a needle shield slidably arranged in relation to the housing, which upon movement releases the force means, wherein the elongated housing is elliptic in cross-section and has a short axis and a long axis, the long axis is larger than the diameter of the needle shield, thereby creating a space between the housing and the needle shield on both sides, and the needle shield is arranged with slots in which fit a front end surface of the housing at the short axis, whereby the needle shield is locked from movement, and the front end of the housing is deformable such that when a user presses in the area of the large axis in a radial direction, the front end surface of the housing at the short axis moves out of the slots of the needle shield, thereby freeing it for movement.

4. The device of claim 3, wherein the activating means comprises flexible locking means arranged to hold the plunger rod with the compression spring in a tensioned state, which flexible locking means are released when the needle shield is moved a certain distance, releasing the plunger rod.

5. A device for delivering a dose of medicament, comprising:
    a generally elongated housing having a front end and a rear end,
    a container containing medicament to be injected through a needle,
    force means comprising a plunger rod and a compression spring arranged within the plunger rod, wherein the plunger rod is arranged to act on a stopper disposed in the container such that, upon activation of the force means, the container and the needle are moved for penetration and for subsequently expelling medicament through the needle, and
    activating means comprising a needle shield slidably arranged in relation to the housing, which upon movement releases the force means, wherein the elongated housing is elliptic in cross-section and has a short axis and a long axis, the long axis is larger than the diameter of the needle shield, thereby creating a space between the housing and the needle shield on both sides, and the needle shield is arranged with slots in which fit a front end surface of the housing at the short axis, whereby the needle shield is locked from movement, and the activating means comprises stop ledges co-acting with ledges on the plunger rod to hold the plunger rod with the compression spring in a tensioned state, which stop ledges are arranged on a rotatable component and means arranged on the needle shield capable of rotating the rotatable component when the needle shield is moved a certain distance, rotating the stop ledges out of contact with the ledges on the plunger rod, releasing the plunger rod.

6. The device of claim 5, wherein the needle shield is arranged with protrusions co-acting with inclined ridges on the rotatable component causing the rotatable component to rotate when the needle shield is moved.

7. The device of claim 3, further comprising means for pushing the needle shield to an extended position covering the needle when the device is withdrawn from an injection site, and means for locking the needle shield in the extended position.

8. The device of claim 3, wherein the activating means comprises flexible locking means arranged to hold the plunger rod with the compression spring in a tensioned state, which flexible locking means are released when the needle shield is moved a certain distance, releasing the plunger rod.

9. The device of claim 3, wherein the activating means comprises stop ledges co-acting with ledges on the plunger rod to hold the plunger rod with the compression spring in a tensioned state, which stop ledges are arranged on a rotatable component and means arranged on the needle shield capable of rotating the rotatable component when the needle shield is moved a certain distance, rotating the stop ledges out of contact with the ledges on the plunger rod, releasing the plunger rod.

10. The device of claim 9, wherein the needle shield is arranged with protrusions co-acting with inclined ridges on the rotatable component causing the rotatable component to rotate when the needle shield is moved.

11. The device of claim 3, further comprising means for pushing the needle shield to an extended position covering the needle when the device is withdrawn from an injection site, and means for locking the needle shield in the extended position.

* * * * *